US012746351B2

(12) United States Patent
Lange et al.

(10) Patent No.: US 12,746,351 B2
(45) Date of Patent: Sep. 29, 2026

(54) HIGH BARRIER POWDER CAPSULE

(71) Applicant: PHILIP MORRIS PRODUCTS S.A., Neuchâtel (CH)

(72) Inventors: Ross Lange, Neuchâtel (CH); Cristian Neagu, Epalinges (CH); Cesare Lorenzetti, Boudry (CH)

(73) Assignee: Philip Morris Products S.A., Neuchâtel (CH)

( * ) Notice: Subject to any disclaimer, the term of this patent is extended or adjusted under 35 U.S.C. 154(b) by 984 days.

(21) Appl. No.: 17/801,857

(22) PCT Filed: Feb. 23, 2021

(86) PCT No.: PCT/IB2021/051522

§ 371 (c)(1),
(2) Date: Aug. 24, 2022

(87) PCT Pub. No.: WO2021/171180

PCT Pub. Date: Sep. 2, 2021

(65) Prior Publication Data

US 2023/0085911 A1 Mar. 23, 2023

(30) Foreign Application Priority Data

Feb. 26, 2020 (EP) .................................... 20159624

(51) Int. Cl.
*A61M 15/00* (2006.01)
*A61J 3/07* (2006.01)

(52) U.S. Cl.
CPC ............ *A61M 15/003* (2014.02); *A61J 3/072* (2013.01); *A61M 2202/064* (2013.01); *A61M 2205/0238* (2013.01); *A61M 2207/00* (2013.01)

(58) Field of Classification Search
CPC ............................ A61K 9/4808; A61K 9/4891
See application file for complete search history.

(56) References Cited

U.S. PATENT DOCUMENTS

| | | | | |
|---|---|---|---|---|
| 3,084,128 A * | 4/1963 | Stillwagon | C09D 191/08 | 524/488 |
| 3,497,129 A * | 2/1970 | Stein | B65D 31/02 | 493/193 |
| 2003/0106827 A1* | 6/2003 | Cheu | B65D 81/24 | 206/531 |

FOREIGN PATENT DOCUMENTS

| | | |
|---|---|---|
| GB | 2425115 | 10/2006 |
| JP | 3913532 B2 * | 5/2007 |
| WO | 21090186372 | 10/2019 |

OTHER PUBLICATIONS

English machine translation of JP-3913532-B2 made on Oct. 30, 2025. (Year: 2025).*
European Search Report for EP 20159624.4 issued by the European Patent Office on Jun. 12, 2020; 8 pgs.
International Search Report and Written Opinion for PCT/IB2021/051522, Apr. 26, 2022 issued by the European Patent Office; 15 pgs.
International Preliminary Report on Patentability for PCT/IB2021/051522, issued by the European Patent Office, Feb. 11, 2022; 12 pgs.

* cited by examiner

*Primary Examiner* — Michael B. Pallay
(74) *Attorney, Agent, or Firm* — Mueting Raasch Group

(57) ABSTRACT

A capsule article (100) includes a polymeric body (110) extending along a longitudinal axis from a first end to a second end and defining a capsule cavity (105) containing powder, and a metal foil (120) and a sealant layer (130) covering an outer surface of the polymeric body. A method of forming a hermetic capsule includes the steps of wrapping a capsule, with a metal foil; and enclosing the capsule with a sealant layer to form a hermetic barrier enclosing the capsule.

16 Claims, 1 Drawing Sheet

HIGH BARRIER POWDER CAPSULE

This application is the § 371 U.S. National Stage of International Application No. PCT/IB2021/051522, filed 23 Feb. 2021, which claims the benefit of European Application No. 20159624.4, filed 26 Feb. 2020, the disclosures of which are incorporated herein by reference.

The present disclosure relates to high barrier capsule containing powder. The high barrier capsule is covered by a metal foil and a sealant layer. The metal foil and a sealant layer cooperate to inhibit the transfer of water or moisture to the contents of the high barrier capsule.

Capsules generally possess poor water barrier properties. Therapeutic dry powders are often formed of materials that are hygroscopic and are degraded by contact with water or moisture. These capsules are often sealed in non-biodegradable packaging. This non-biodegradable packaging may increase the cost and complexity of the manufacture of these capsules and associated inhaler systems.

It would be desirable to provide a capsule that inhibits or prevents the transfer of water or moisture into the capsule cavity. It would be desirable to provide a high barrier capsule that may be biodegradable. It would be desirable that the high barrier capsule maintain aerodynamics of the capsule and allow the high barrier capsule to rotate or spin during consumption within an inhaler device. It would be desirable that the high barrier capsule be cost effective, simple and easy to apply onto the capsule for inhalable dry powders. It would be desirable that the high barrier capsule be formed of food safe materials.

According to an aspect of the present invention, there is provided a capsule article comprising a polymeric body extending along a longitudinal axis from a first end to a second end and defining a capsule cavity containing powder. A metal foil and a sealant layer cover an outer surface of the polymeric body.

Advantageously, the metal foil and a sealant layer cooperate for form a protective barrier enclosing the capsule. The metal foil and a sealant layer form a low-profile protective barrier enclosing the capsule that may maintain the shape of the capsule and maintain the aerodynamic properties of the capsule.

The capsule article may include the sealant layer contacting the metal foil and the metal foil separating the sealant layer from the polymeric body. Coating the metal foil with the sealant layer may be advantageous to fill holes or cracks formed in the metal foil or formed during the metal foil wrapping process.

The capsule article may include the sealant layer contacting the metal foil and the sealant layer separating the metal foil from the polymeric body. The sealant layer may aid in adhering the metal foil to the polymeric body. The sealant layer may advantageously fill holes in the metal foil layer. Having the metal foil form an outer layer of the capsule article may further stabilize the capsule article in higher temperature storage or transport. Having the metal foil form an outer layer of the capsule article may prevent the capsule article from becoming sticky increasing outer surface friction in higher temperature storage or transport.

The capsule article may include the sealant layer contacting the metal foil and separating the metal foil from the polymeric body and a second sealant layer contacting the metal foil and metal foil separates the sealant layer from the second sealant layer. Sandwiching the metal foil between two sealant layers may improve the barrier properties while advantageously filling holes or cracks formed during the metal foil wrapping process with the second sealing layer.

The capsule article polymeric body may define an obround shape and the metal foil and a sealant layer define an obround shape. The metal foil and sealant layer mimicking the outer shape of the capsule may advantageously maintain the capsule aerodynamics and allow the high barrier capsule to spin or rotate during consumption.

The capsule article sealant layer may have a melting temperature of about 100 degrees Celsius or less, or in a range from about 40 degrees Celsius to about 80 degrees Celsius. The powder contained within the capsule cavity may degrade at temperatures above 100 degrees Celsius, or above 80 degrees Celsius, thus applying a liquid or flowable sealant onto the capsule or metal foil advantageously occurs at temperature of about 100 degrees Celsius or less.

The capsule article sealant layer may have a thickness of about 2 micrometres to about 15 micrometres, or from about 3 micrometres to about 10 micrometres. Sealant thicknesses less than 15 micrometres or less than 10 micrometres may maintain the capsule aerodynamics and allow the high barrier capsule to spin or rotate during consumption while still cooperating with the metal foil to form a hermetic barrier around the capsule cavity.

The capsule article sealant layer may comprise a wax material. The capsule article sealant layer may comprise a microcrystalline wax. Wax materials may be food safe material and may also be biodegradable materials.

The capsule article metal foil may have a thickness in a range from about 2 micrometres to about 10 micrometres, or from about 4 micrometres to about 8 micrometres. Metal foil thicknesses less than 10 micrometres or less than 8 micrometres may maintain the capsule aerodynamics and allow the high barrier capsule to spin or rotate during consumption while still cooperating with the metal foil to form a hermetic barrier around the capsule cavity.

The capsule article metal foil may comprise aluminium foil. Aluminium foil may be food safe material and may also be biodegradable materials.

The capsule article metal foil and sealant layer and optional second sealant layer may cooperate to form a hermetic barrier enclosing the polymeric body or capsule cavity. Combining a metal foil with a sealant layer has been found to advantageously form a hermetic barrier with a reducing thickness and maintaining the capsule aerodynamics and allow the high barrier capsule to spin or rotate during consumption while still cooperating with the metal foil to form a hermetic barrier around the capsule cavity.

According to another aspect of the present invention, there is provided a method of forming a hermetic capsule comprising the steps of: wrapping a capsule, with a metal foil; and enclosing the capsule with a sealant layer to form a hermetic barrier enclosing the capsule.

Advantageously, wrapping articles with metal foil may be performed at high speeds with high definition or accuracy. The metal foil and a sealant layer cooperate for form a protective barrier enclosing the capsule. The metal foil and a sealant layer form a low-profile protective barrier enclosing the capsule that may maintain the shape of the capsule and maintain the aerodynamic properties of the capsule. The metal foil and a sealant layer may cooperate to provide a stronger moisture barrier than the additive barrier effect of each layer.

The method may comprise enclosing the metal foil with the sealant layer. Enclosing or coating the metal foil with the sealant layer may be advantageous to fill holes or cracks formed during the metal foil wrapping process.

The method may comprise enclosing the capsule with the sealant layer and then wrapping the sealant layer with the meal foil.

The method may comprise enclosing the capsule with the sealant layer and then wrapping the sealant layer with the meal foil and then enclosing the metal foil with a second sealant layer. Sandwiching the metal foil between two sealant layers may improve the barrier properties while advantageously filling holes or cracks formed during the metal foil wrapping process with the second sealing layer.

The method may comprise enclosing the capsule with the sealant layer at a temperature of about 100 degrees Celsius or less, or in a range from about 40 degrees Celsius to about 80 degrees Celsius. The powder contained within the capsule cavity may degrade at temperatures above 100 degrees Celsius, or above 80 degrees Celsius, thus applying a liquid or flowable sealant onto the capsule or metal foil advantageously occurs at temperature of about 100 degrees Celsius or less.

The method may comprise applying sealant or the sealant layer to the metal foil prior to wrapping the metal foil onto the polymeric body of the capsule. The sealant or sealant layer may be disposed on the metal foil before the wrapping step to form a wrapped capsule. The metal foil and sealant layer may form a laminate that may be wrapped onto the capsule. This sealant metal foil laminate may have a thickness or uniform thickness in a range from about 5 micrometres to about 25 micrometres, or from about 10 micrometres to about 20 micrometres.

The wrapped capsule may then be heated to a temperature above a melting temperature of the sealant layer to form the hermetic barrier enclosing the capsule. When the sealant is pre-applied on the surface of the foil, the sealing process may be advantageously performed contacting the wrapped capsule with hot surfaces, hot air or by induction heating.

The high barrier capsule may be utilized in an inhaler device having a capsule cavity. Air flow management through a capsule cavity of the inhaler device may cause a high barrier capsule contained therein to rotate during inhalation and consumption. The high barrier capsule may contain particles containing nicotine (also referred to as "nicotine powder" or "nicotine particles") and optionally particles comprising flavour (also referred to as "flavour particles"). These particles may be hygroscopic and detrimentally agglomerate or clump together if water of moisture contacts these particles. Rotation of the pierced high barrier capsule may suspend and aerosolize the nicotine particles released from the pierced high barrier capsule into the inhalation air moving through the inhaler device. The optional flavour particles may be larger than the nicotine particles and may assist in transporting the nicotine particles into the lungs of the user while the flavour particles preferentially remain in the mouth or buccal cavity of the user. The nicotine particles and optional flavor particles may be delivered with the inhaler device at inhalation or air flow rates that are within conventional smoking regime inhalation or air flow rates.

The term "melting temperature value" refers to the temperature value, at one atmosphere pressure, or standard pressure, that the material begins to flow without applying any external force other than gravity and air pressure.

The term "wax material" refers to a moldable substance of low molecular weight that may be of natural or synthetic origin. Within the framework of this application the wax is a substance or mixture of substances with a molecular weight lower than about 7000 Daltons. Examples are natural paraffins, synthetic paraffins, microcrystalline waxes, low molecular weight polymers of ethylene, propylene or copolymers of the same with acrylic monomers such as acrylic or methacrylic acid and their esters. A variety of copolymers of ethylene, propylene and vinyl acetate are also known.

Other waxes of natural origin include carnauba wax, candelilla wax, dammar gum/wax, sugarcane wax, palmitin, stearin, and the like.

With reference to the afore mentioned application a wax can be a formulation of several components such as those listed and may also contain a minor amount of high molecular weight polymers with the purpose of adjusting the rheology and mechanical properties of the composition.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open-ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful and is not intended to exclude other embodiments from the scope of the disclosure, including the claims.

This disclosure is directed to a high barrier capsule containing powder. The high barrier capsule is covered by a metal foil and a sealant layer. The metal foil and a sealant layer cooperate to inhibit the transfer of water or moisture to the contents of the high barrier capsule.

The high barrier capsule article includes a polymeric body extending along a longitudinal axis from a first end to a second end and defining a capsule cavity containing powder. A metal foil and a sealant layer cover an outer surface of the polymeric body.

The capsule body may be formed of a polymer material. The polymer material may be hydroxypropyl methylcellulose (HPMC). The capsule may be a size 1 to size 4 capsule, or a size 3 capsule. The polymeric body may define an obround shape. The polymeric body may have a single wall thickness in a range from about 75 micrometres to about 120 micrometres, or from about 85 micrometres to about 110 micrometres. The polymeric body may have a longitudinal length from the first end to the second end a value in a range from about 14 millimetres to about 22 millimetres, or from about 15 millimetres to about 20 millimetres. The polymeric body may have an external diameter value in a range from about 4.5 millimetres to about 10 millimetres, or from about 5.5 millimetres to about 6.5 millimetres.

The high barrier capsule article may include the sealant layer contacting the metal foil and the metal foil separating the sealant layer from the polymeric body. The metal foil may completely cover the polymeric body. The sealant layer may completely cover the metal foil. The metal foil may be wrapped onto the first end and second end of the polymeric body. The first end may form a hemispherical surface and the second end may form a hemispherical surface. Wrapping the metal foil onto the first hemispherical end and second hemispherical end may form curved air channels that cooperate with inhalation air to improve the high barrier capsule aerodynamics and rotation or spinning properties during consumption.

The capsule article may include the sealant layer contacting the metal foil and the sealant layer separating the metal foil from the polymeric body. The sealant layer may completely cover the polymeric body. The metal foil may completely cover the sealant layer. The metal foil may be wrapped onto the first end and second end of the polymeric body. The first end may form a hemispherical surface and the second end may form a hemispherical surface. Wrapping the metal foil onto the first hemispherical end and second hemispherical end may form curved air channels that cooperate with inhalation air to improve the high barrier capsule aerodynamics and rotation or spinning properties during consumption. The sealant layer may provide adhesion of metal foil to the polymeric body.

The capsule article may include the sealant layer contacting the metal foil and separating the metal foil from the polymeric body and a second sealant layer contacting the metal foil and metal foil separates the sealant layer from the second sealant layer. he sealant layer may completely cover the polymeric body. The metal foil may completely cover the sealant layer. The metal foil may be wrapped onto the first end and second end of the polymeric body. The first end may form a hemispherical surface and the second end may form a hemispherical surface. Wrapping the metal foil onto the first hemispherical end and second hemispherical end may form curved air channels that cooperate with inhalation air to improve the high barrier capsule aerodynamics and rotation or spinning properties during consumption. The sealant layer may provide adhesion of metal foil to the polymeric body.

The capsule article polymeric body may define an obround shape and the metal foil and a sealant layer define an obround shape. The metal foil and sealant layer mimicking the outer shape of the capsule may advantageously maintain the capsule aerodynamics and allow the high barrier capsule to spin or rotate during consumption.

The capsule article sealant layer may have a melting temperature of about 100 degrees Celsius or less, or in a range from about 40 degrees Celsius to about 80 degrees Celsius. The powder contained within the capsule cavity may degrade at temperatures above 100 degrees Celsius, or above 80 degrees Celsius, thus applying a liquid or flowable sealant onto the capsule or metal foil advantageously occurs at temperature of about 100 degrees Celsius or less.

The capsule article sealant layer may have a thickness of about 2 micrometres to about 15 micrometres, or from about 3 micrometres to about 10 micrometres. Sealant thicknesses less than 15 micrometres or less than 10 micrometres may maintain the capsule aerodynamics and allow the high barrier capsule to spin or rotate during consumption while still cooperating with the metal foil to form a hermetic barrier around the capsule cavity.

The capsule article sealant layer may comprise wax materials, aliphatic polyesters and mixtures with paraffin wax preferably applied from a water dispersion. The capsule article sealant layer may comprise cellulose esters and mixtures with paraffin wax preferably applied from water or alcohol dispersions. The capsule article sealant layer may be prepared from organic solvent dispersions of cellulose derivatives (esters, ethers or nitrates) and paraffin. The capsule article sealant layer may comprise vegetal wax-based formulations (such as, carnauba wax, candelilla wax, dammar gum/wax, sugarcane wax, palmitin, stearin, and the like). This sealant layer may be prepared by dispersion coating, applied from solutions, hot melt coating or extrusion coating.

The capsule article sealant layer may comprise adhesion promoters such as, polymers or material having carboxylic acid functionalities, or other substances such as anti-blocking and slip agents.

The capsule article sealant layer formulations may be adapted by a skilled person with a view at improving adhesion to the polymeric body or the metal foil, adjusting its melting point, and ensuring its biodegradability or compostability.

The capsule article sealant layer may comprise a wax material. The capsule article sealant layer may comprise a microcrystalline wax. Wax materials may be food safe material and may also be biodegradable materials.

Substances such as microcrystalline waxes may also be oxidized to enhance adhesion toward polar substrates.

The capsule article metal foil may have a thickness in a range from about 2 micrometres to about 10 micrometres, or from about 4 micrometres to about 8 micrometres. Metal foil thicknesses less than 10 micrometres or less than 8 micrometres may maintain the capsule aerodynamics and allow the high barrier capsule to spin or rotate during consumption while still cooperating with the metal foil to form a hermetic barrier around the capsule cavity. Holes or pinholes may be present in this metal foil as a consequence of the manufacturing or article assembly process.

The capsule article metal foil may comprise aluminium foil. Aluminium foil may be food safe material and may also be biodegradable materials.

The capsule article metal foil and sealant layer and optional second sealant layer may cooperate to form a moisture or hermetic barrier enclosing the polymeric body or capsule cavity. Combining a metal foil with a sealant layer has been found to advantageously form a moisture or hermetic barrier that may be greater than the additive barrier effect of each layer individually while reducing thickness and maintaining the capsule aerodynamics and to allow the high barrier capsule to spin or rotate during consumption while still cooperating with the metal foil to form a synergistic moisture hermetic barrier around the capsule cavity.

The capsule article metal foil and sealant layer may have a total thickness in a range from about 4 micrometres or about 15 micrometres, or from about 8 micrometres or about 12 micrometres, or about 10 micrometres.

The capsule article metal foil and sealant layer and second sealant layer may have a total thickness in a range from about 6 micrometres or about 25 micrometres, or from about 10 micrometres or about 20 micrometres, or about 15 micrometres.

The disclosure is directed to a method of forming a hermetic capsule including the steps of: wrapping a capsule, with a metal foil; and enclosing the capsule with a sealant layer to form a hermetic barrier enclosing the capsule. The high barrier powder capsule may have a water transmission rate measured at 38 degrees Celsius and 90% relative humidity of 0.02 grams/($m^2$×day) or less.

The method may include enclosing the metal foil with the sealant layer. Enclosing or coating the metal foil with the sealant layer may be advantageous to fill holes or cracks formed during the metal foil wrapping process.

The method may include enclosing the capsule with the sealant layer and then wrapping the sealant layer with the meal foil. An outer metal foil layer or surface may ensure a low friction outer surface even at elevated environmental temperatures. The sealant layer may adhere the metal foil to the capsule polymeric layer while filling holes or pinholes present in the metal foil.

The method may include enclosing the capsule with the sealant layer and then wrapping the sealant layer with the meal foil and then enclosing the metal foil with a second sealant layer. Sandwiching the metal foil between two sealant layers may improve the barrier properties while advantageously filling holes or cracks formed during the metal foil wrapping process with the second sealing layer.

The method may include enclosing the capsule with the sealant layer at a temperature of about 100 degrees Celsius or less, or in a range from about 40 degrees Celsius to about 80 degrees Celsius. The powder contained within the capsule cavity may degrade at temperatures above 100 degrees Celsius, or above 80 degrees Celsius, thus applying a liquid or flowable sealant onto the capsule or metal foil advantageously occurs at temperature of about 100 degrees Celsius or less.

The high barrier capsule may contain pharmaceutically active particles. For instance, the pharmaceutically active particles may comprise nicotine. The pharmaceutically active particles may have a mass median aerodynamic diameter of about 5 micrometres or less, or in a range from about 0.5 micrometres to about 4 micrometres, or in a range from about 1 micrometre to about 3 micrometres.

The high barrier capsule may contain nicotine particles comprising nicotine (also referred to as "nicotine powder" or "nicotine particles") and optionally particles comprising flavour (also referred to as "flavour particles"). The high barrier capsule may contain a predetermined amount of nicotine particles and optional flavour particles. The high barrier capsule may contain enough nicotine particles to provide at least 2 inhalations or "puffs", or at least about 5 inhalations or "puffs", or at least about 10 inhalations or "puffs". The high barrier capsule may contain enough nicotine particles to provide from about 5 to about 50 inhalations or "puffs", or from about 10 to about 30 inhalations or "puffs". Each inhalation or "puff" may deliver from about 0.1 mg to about 3 mg of nicotine particles to the lungs of the user or from about 0.2 mg to about 2 mg of nicotine particles to the lungs of the user or about 1 mg of nicotine particles to the lungs of the user.

The nicotine particles may have any useful concentration of nicotine based on the particular formulation employed. The nicotine particles may have at least about 1% wt nicotine up to about 30% wt nicotine, or from about 2% wt to about 25% wt nicotine, or from about 3% wt to about 20% wt nicotine, or from about 4% wt to about 15% wt nicotine, or from about 5% wt to about 13% wt nicotine. Preferably, about 50 to about 150 micrograms of nicotine may be delivered to the lungs of the user with each inhalation or "puff".

The high barrier capsule may hold or contain at least about 5 mg of nicotine particles or at least about 10 mg of nicotine particles. The capsule may hold or contain less than about 900 mg of nicotine particles, or less than about 300 mg of nicotine particles, or less than 150 mg of nicotine particles. The capsule may hold or contain from about 5 mg to about 300 mg of nicotine particles or from about 10 mg to about 200 mg of nicotine particles.

When flavour particles are blended or combined with the nicotine particles within the capsule, the flavour particles may be present in an amount that provides the desired flavour to each inhalation or "puff" delivered to the user.

The nicotine particles may have any useful size distribution for inhalation delivery preferentially into the lungs of a user. The capsule may include particles other than the nicotine particles. The nicotine particles and the other particles may form a powder system.

The high barrier capsule may hold or contain at least about 5 mg of a dry powder (also referred to as a powder system) or at least about 10 mg of a dry powder. The high barrier capsule may hold or contain less than about 900 mg of a dry powder, or less than about 300 mg of a dry powder, or less than about 150 mg of a dry powder. The high barrier capsule may hold or contain from about 5 mg to about 300 mg of a dry powder, or from about 10 mg to about 200 mg of a dry powder, or from about 25 mg to about 100 mg of a dry powder.

The dry powder or powder system may have at least about 40%, or at least about 60%, or at least about 80%, by weight of the powder system comprised in nicotine particles having a particle size of about 5 micrometres or less, or in a range from about 1 micrometre to about 5 micrometres.

The particles comprising nicotine may have a mass median aerodynamic diameter of about 5 micrometres or less, or in a range from about 0.5 micrometres to about 4 micrometres, or in a range from about 1 micrometres to about 3 micrometres or in a range from about 1.5 micrometres to about 2.5 micrometres. The mass median aerodynamic diameter is preferably measured with a cascade impactor.

The particles comprising flavour may have a mass median aerodynamic diameter of about 20 micrometres or greater, or about 50 micrometres or greater, or in a range from about 50 to about 200 micrometres, or from about 50 to about 150 micrometres. The mass median aerodynamic diameter is preferably measured with a cascade impactor.

Nicotine in the powder system or nicotine particles may be a pharmaceutically acceptable free-base nicotine, or nicotine salt or nicotine salt hydrate. Useful nicotine salts or nicotine salt hydrates include nicotine pyruvate, nicotine citrate, nicotine aspartate, nicotine lactate, nicotine bitartrate, nicotine salicylate, nicotine fumarate, nicotine monopyruvate, nicotine glutamate or nicotine hydrochloride, for example. The compound combining with nicotine to form the salt or salt hydrate may be chosen based on its expected pharmacological effect.

The nicotine particles preferably include an amino acid. Preferably, the amino acid may be leucine such as L-leucine. Providing an amino acid such as L-leucine with the particles comprising nicotine, may reduce adhesion forces of the particles comprising nicotine and may reduce attraction between nicotine particles and thus reduce agglomeration of nicotine particles. Similarly, adhesion forces to particles comprising flavour may also be reduced thus agglomeration of nicotine particles with flavour particles is also reduced. The powder system described herein thus may be a free-flowing material and possess a stable relative particle size of each powder component even when the nicotine particles and the flavour particles are combined.

Preferably, the nicotine may be a surface modified nicotine salt where the nicotine salt particle comprises a coated or composite particle. A preferred coating or composite material may be L-leucine. One particularly useful nicotine particle may be nicotine bitartrate with L-leucine.

The powder system may include a population of flavour particles. The flavour particles may have any useful size distribution for inhalation delivery selectively into the mouth or buccal cavity of a user.

The particles comprising flavour may include a compound to reduce adhesion forces or surface energy and resulting agglomeration. The flavour particle may be surface modified with an adhesion reducing compound to form a coated flavour particle. One preferred adhesion reducing compound may be magnesium stearate. Providing an adhesion reducing compound such as magnesium stearate with the flavour particle, especially coating the flavour particle, may reduce adhesion forces of the particles comprising flavour and may reduce attraction between flavour particles and thus reduce agglomeration of flavour particles. Thus, agglomeration of flavour particles with nicotine particles may also be reduced. The powder system described herein thus may possess a stable relative particle size of the particles comprising nicotine and the particles comprising flavour even when the nicotine particles and the flavour particles are combined. The powder system preferably may be free flowing.

The nicotine particles and flavour particles may be combined in any useful relative amount so that the flavour particles are detected by the user when consumed with the nicotine particles. Preferably, the nicotine particles and a flavour particles form at least about 90% wt or at least about 95% wt or at least about 99% wt or 100% wt of the total weight of the powder system.

The invention is defined in the claims. However, below there is provided a non-exhaustive listing of non-limiting examples. Amy one or more of the features of these examples may be combined with any one or more features of another example, embodiment, or aspect described herein.

Example Ex1: A capsule article comprising: a polymeric body extending along a longitudinal axis from a first end to a second end and defining a capsule cavity containing powder; and a metal foil and a sealant layer covering an outer surface of the polymeric body.

Example Ex2. The capsule article of example Ex1, wherein the sealant layer contacts the metal foil and the metal foil separates the sealant layer from the polymeric body.

Example Ex3. The capsule article of example Ex1, wherein the sealant layer contacts the metal foil and the sealant layer separates the metal foil from the polymeric body.

Example Ex4. The capsule article of example Ex1, wherein the sealant layer contacts the metal foil and the sealant layer separates the metal foil from the polymeric body and a second sealant layer contacts the metal foil and the metal foil separates the sealant layer from the second sealant layer.

Example Ex5. The capsule article of any preceding example, wherein the polymeric body defines an obround shape and the metal foil and a sealant layer define an obround shape.

Example Ex6. The capsule article of any preceding example, wherein the sealant layer has a melting temperature of about 100 degrees Celsius or less, or in a range from about 40 degrees Celsius to about 80 degrees Celsius.

Example Ex7. The capsule article of any preceding example, wherein the sealant layer has a thickness of about 2 micrometres to about 15 micrometres, or from about 3 micrometres to about 10 micrometres.

Example Ex8. The capsule article of any preceding example, wherein the sealant layer comprises a wax material.

Example Ex9. The capsule article of any preceding example, wherein the sealant layer comprises a microcrystalline wax.

Example Ex10. The capsule article of any preceding example, wherein the metal foil has a thickness in a range from about 2 micrometres to about 10 micrometres, or from about 4 micrometres to about 8 micrometers.

Example Ex11. The capsule article of any preceding example, wherein the metal foil comprises aluminum foil.

Example Ex12. The capsule article of any preceding Example, wherein the sealant layer and metal foil cooperate to form a hermetic barrier enclosing the polymeric body or capsule cavity.

Example Ex13. A method of forming a hermetic capsule comprising the steps of: wrapping a capsule, with a metal foil; and enclosing the capsule with a sealant layer to form a hermetic barrier enclosing the capsule.

Example Ex14. The method according to example Ex13, wherein the enclosing step comprises enclosing the metal foil with the sealant layer.

Example Ex15. The method according to example Ex13, wherein the enclosing step comprises enclosing the capsule with the sealant layer and then wrapping the sealant layer with the meal foil.

Example Ex16. The method according to example Ex15, wherein the enclosing step comprises enclosing the metal foil with a second sealant layer.

Example Ex17. The method according to example Ex13, to example Ex16 further comprising disposing the sealant layer onto the metal foil before the wrapping step to form a wrapped capsule.

Example Ex18. The method according to example Ex17, further comprising heating the wrapped capsule to a temperature above a melting temperature of the sealant layer to form the hermetic barrier enclosing the capsule.

The Examples will now be further described with reference to the figures in which.

Figure 1:
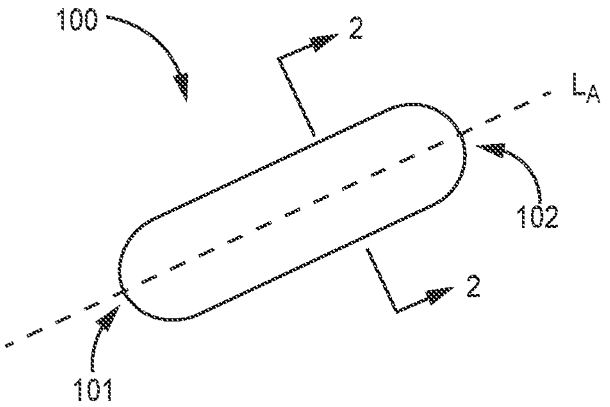
FIG. 1 is a perspective schematic diagram of an illustrative high barrier capsule.

The schematic drawings are not necessarily to scale and are presented for purposes of illustration and not limitation. The drawings depict one or more aspects described in this disclosure. However, it will be understood that other aspects not depicted in the drawing fall within the scope and spirit of this disclosure.

Figure 2:
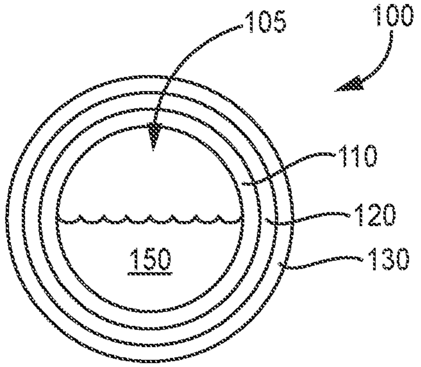
FIG. 2 is a cross-sectional schematic diagram of an illustrative high barrier capsule taken along line 2-2 of FIG. 1.
Figure 3:
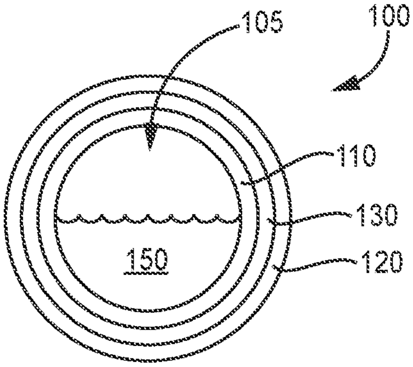
FIG. 3 is a cross-sectional schematic diagram of another illustrative high barrier capsule taken along line 2-2 of FIG. 1.
Figure 4:
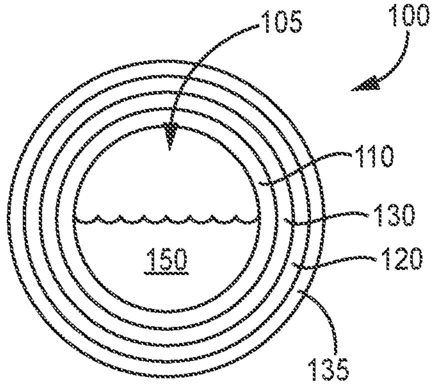
FIG. 4 is a cross-sectional schematic diagram of another illustrative high barrier capsule taken along line 2-2 of FIG. 1.

FIG. 1 is a perspective schematic diagram of an illustrative high barrier capsule 100. FIG. 2 to FIG. 4 are alternate configurations of the high barrier capsule 100. The high barrier capsule 100 includes a polymeric body 110 extending along a longitudinal axis $L_A$ from a first end 101 to a second end 102 defining a capsule cavity 105 containing powder 150. A metal foil 120 and a sealant layer 130 cover an outer surface of the polymeric body 110.

FIG. 2 is a cross-sectional schematic diagram of an illustrative high barrier capsule 100. The sealant layer 130 contacts the metal foil 120 and the sealant layer 130 separates the metal foil 120 from the polymeric body 110.

FIG. 3 is a cross-sectional schematic diagram of another illustrative high barrier capsule 100. The sealant layer 130 contacts the metal foil 120 and the metal foil 120 separates the sealant layer 130 from the polymeric body 110.

FIG. 4 is a cross-sectional schematic diagram of another illustrative high barrier capsule high barrier capsule 100. The sealant layer 130 contacts the metal foil 120 and the sealant layer 130 separates the metal foil 130 from the polymeric body 110 and a second sealant layer 135 contacts the metal foil 120 and the metal foil 120 separates the sealant layer 130 from the second sealant layer 135.

For the purpose of the present description and of the appended claims, except where otherwise indicated, all numbers expressing amounts, quantities, percentages, and so forth, are to be understood as being modified in all instances by the term "about". Also, all ranges include the maximum and minimum points disclosed and include any intermediate ranges therein, which may or may not be specifically enumerated herein. In this context, therefore, a number A is understood as A±2% of A. Within this context, a number A may be considered to include numerical values that are within general standard error for the measurement of the property that the number A modifies. The number A, in some instances as used in the appended claims, may deviate by the percentages enumerated above provided that the amount by which A deviates does not materially affect the basic and novel characteristic(s) of the claimed invention. Also, all ranges include the maximum and minimum points disclosed and include any intermediate ranges therein, which may or may not be specifically enumerated herein.

The invention claimed is:

1. A capsule article comprising:

a polymeric body extending along a longitudinal axis from a first end to a second end and defining a capsule cavity containing powder; and a metal foil; and a sealant layer; wherein at least one of the sealant layer and the metal foil is disposed directly on and contacting an outer surface of the polymeric body and completely covers the outer surface of the polymeric body, wherein the sealant layer and the metal foil cooperate to form a hermetic barrier enclosing the polymeric body or the capsule cavity.

2. The capsule article of claim 1, wherein the sealant layer contacts the metal foil and the metal foil separates the sealant layer from the polymeric body.

3. The capsule article of claim 1, wherein the sealant layer contacts the metal foil and the sealant layer separates the metal foil from the polymeric body.

4. The capsule article of claim 3, wherein the sealant layer comprises a wax material, and the metal foil comprises aluminum foil, and the sealant layer has a thickness from about 3 micrometres to about 10 micrometres, and the metal foil has a thickness in a range from about 4 micrometres to about 8 micrometres.

5. The capsule article of claim 1, wherein the sealant layer contacts the metal foil and the sealant layer separates the metal foil from the polymeric body and a second sealant layer contacts the metal foil and the metal foil separates the sealant layer from the second sealant layer.

6. The capsule article of claim 1, wherein the polymeric body defines an obround shape and the metal foil and a sealant layer define an obround shape.

7. The capsule article of claim 1, wherein the sealant layer has a melting temperature of about 100 degrees Celsius or less.

8. The capsule article of claim 1, wherein the sealant layer has a thickness of about 2 micrometres to about 15 micrometres.

9. The capsule article of claim 1, wherein the sealant layer comprises a wax material.

10. The capsule article of claim 1, wherein the sealant layer comprises a microcrystalline wax.

11. The capsule article of claim 1, wherein the metal foil has a thickness in a range from about 2 micrometres to about 10 micrometres.

12. The capsule article of claim 1, wherein the metal foil comprises aluminum foil.

13. The capsule article of claim 1, wherein the sealant layer has a melting temperature in a range from about 40 degrees Celsius to about 80 degrees Celsius.

14. The capsule article of claim 1, wherein the sealant layer has a thickness from about 3 micrometres to about 10 micrometres.

15. The capsule article of claim 1, wherein the metal foil has a thickness in a range from about 4 micrometres to about 8 micrometres.

16. The capsule article of claim 1, wherein the sealant layer comprises a wax material, and the metal foil comprises aluminum foil.

* * * * *